United States Patent
Shishimi et al.

(10) Patent No.: US 12,116,338 B2
(45) Date of Patent: Oct. 15, 2024

(54) ALDEHYDE COMPOUND AND METHOD FOR PRODUCING SAME, AND FRAGRANCE COMPOSITION

(71) Applicant: MITSUBISHI GAS CHEMICAL COMPANY, INC., Chiyoda-ku (JP)

(72) Inventors: Toru Shishimi, Okayama (JP); Yutaka Matsuura, Niigata (JP); Shinichi Nagao, Kanagawa (JP)

(73) Assignee: MITSUBISHI GAS CHEMICAL COMPANY, INC., Chiyoda-ku (JP)

( * ) Notice: Subject to any disclaimer, the term of this patent is extended or adjusted under 35 U.S.C. 154(b) by 0 days.

(21) Appl. No.: 17/768,722

(22) PCT Filed: Oct. 16, 2020

(86) PCT No.: PCT/JP2020/039006
§ 371 (c)(1),
(2) Date: Apr. 13, 2022

(87) PCT Pub. No.: WO2021/075517
PCT Pub. Date: Apr. 22, 2021

(65) Prior Publication Data
US 2024/0158331 A1    May 16, 2024

(30) Foreign Application Priority Data
Oct. 17, 2019    (JP) ................................ 2019-190252

(51) Int. Cl.
| | | |
|---|---|---|
| C07C 47/228 | (2006.01) | |
| C07C 45/45 | (2006.01) | |
| C07C 45/62 | (2006.01) | |
| C07C 47/542 | (2006.01) | |
| C11B 9/00 | (2006.01) | |

(52) U.S. Cl.
CPC ............ *C07C 47/228* (2013.01); *C07C 45/45* (2013.01); *C07C 45/62* (2013.01); *C07C 47/542* (2013.01); *C11B 9/0061* (2013.01)

(58) Field of Classification Search
CPC ..... C07C 47/542; C07C 47/228; C07C 45/45; C07C 45/62; C11B 9/0061
See application file for complete search history.

(56) References Cited

U.S. PATENT DOCUMENTS

| | | | |
|---|---|---|---|
| 9,656,938 B2* | 5/2017 | Goeke | ................... C07C 47/228 |
| 10,443,018 B2* | 10/2019 | Baumgartner | ........ C07C 47/228 |
| 2016/0075627 A1 | 3/2016 | Goeke et al. | |
| 2016/0369205 A1 | 12/2016 | Goeke et al. | |
| 2017/0298291 A1 | 10/2017 | Baumgartner et al. | |

FOREIGN PATENT DOCUMENTS

| | | |
|---|---|---|
| JP | 2016-523828 A | 8/2016 |
| JP | 2016-530227 A | 9/2016 |
| JP | 2018-502057 A | 1/2018 |
| JP | 2018-138550 A | 9/2018 |
| RU | 2 669 029 C1 | 10/2018 |

OTHER PUBLICATIONS

International Search Report issued Dec. 1, 2020 in PCT/JP2020/039006, filed on Oct. 16, 2020, 2 pages.

* cited by examiner

*Primary Examiner* — Sikarl A Witherspoon
(74) *Attorney, Agent, or Firm* — Oblon, McClelland, Maier & Neustadt, L.L.P.

(57) ABSTRACT

Provided are a novel aldehyde compound suitable for a fragrance and a fragrance ingredient, or a raw material thereof, and a method for producing the aldehyde compound, as well as a fragrance composition containing the aldehyde compound as an active ingredient, and use of the aldehyde compound as a fragrance.
A compound represented by Formula (1):

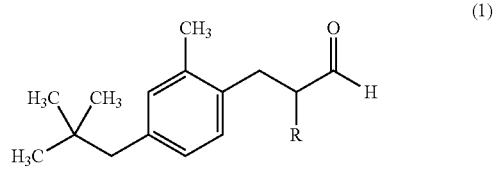

where in Formula (1), R is a hydrogen atom or a methyl group.

6 Claims, No Drawings

ALDEHYDE COMPOUND AND METHOD FOR PRODUCING SAME, AND FRAGRANCE COMPOSITION

CROSS-REFERENCE TO RELATED APPLICATIONS

The present application is a 35 U.S.C. § 371 national stage application of International patent application PCT/JP2020/039006, filed Oct. 16, 2020, which is based on and claims the benefit of priority to Japanese Application No. 2019-190252, filed Oct. 17, 2019. The entire contents of these applications are incorporated herein by reference.

TECHNICAL FIELD

The present invention relates to a novel, first aldehyde compound suitable as a fragrance and a method for producing the same, and a fragrance composition containing the aldehyde compound, and additionally a second aldehyde compound suitable as a raw material of the first aldehyde compound.

BACKGROUND ART

A compound having an aroma and a flavor is extremely useful as a fragrance component, and attention has been focused on use of alkylbenzaldehydes and derivatives thereof in fragrance applications as well as fragrance raw materials.

Patent Document 1 mentions that 3-(4- (sec-butyl)-2 methylphenyl) propanal and 3-(4-isobutyl-2 methyl phenyl)-2 methylpropanal each have an aroma.

Citation List

Patent Documents

Patent Document 1: JP 2018-138550 A

SUMMARY OF INVENTION

Technical Problem

It is an object of the present invention to provide a novel, first aldehyde compound suitable as a fragrance and a fragrance ingredient, and a method for producing the aldehyde compound, as well as a fragrance composition containing the first aldehyde compound as an active ingredient, and use of the compound as a fragrance. Furthermore, another object of the present invention is to provide a novel, second aldehyde compound suitable as a raw material of the first aldehyde compound.

Solution to Problem

The present inventors synthesized various compounds and studied their aromas, and discovered that certain aldehyde compounds had a muguet-tone aroma, thereby arriving at the present invention.

The present invention provides the following aspects <1> to <6>.

<1> A compound represented by Formula (1) below:

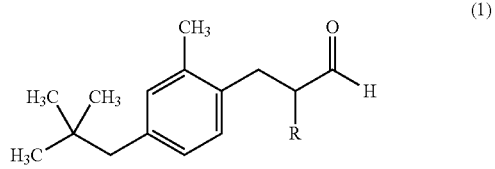

where in Formula (1), R is a hydrogen atom or a methyl group.

<2> The compound described in <1>, wherein R is a hydrogen atom.

<3> A fragrance composition including the compound described in <1> or <2>.

<4> Use of the compound described in <1> or <2> as a fragrance.

<5> A compound represented by Formula (2) below:

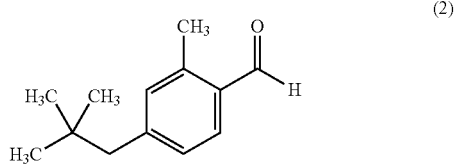

<6> The method for producing a compound represented by Formula (1), the method including, in this order, performing an aldol condensation on a compound represented by Formula (2) with acetaldehyde or propionaldehyde to form a compound represented by Formula (3); and hydrogenating the compound represented by Formula (3) to form a compound represented by Formula (1):

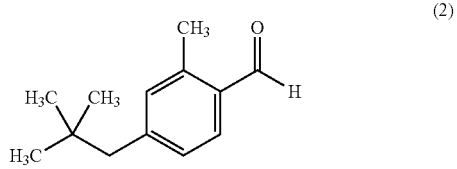

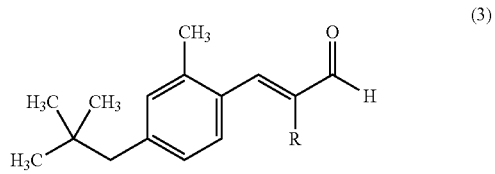

where in Formula (3), R is a hydrogen atom or a methyl group; and

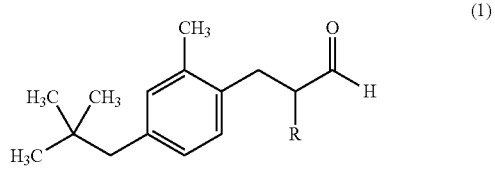

where in Formula (1), R is a hydrogen atom or a methyl group.

Advantageous Effects of Invention

According to the present invention, it is possible to provide a novel, first aldehyde compound suitable as a fragrance and a fragrance ingredient and a method for producing the same, and a fragrance composition containing the first aldehyde compound as an active ingredient, and use of the compound as a fragrance. Furthermore, according to the present invention, it is possible to provide a novel, second aldehyde compound suitable as a raw material of the first aldehyde compound.

DESCRIPTION OF EMBODIMENTS

The present invention will be described below using embodiments. Note that in the following descriptions, notations of "from A to B" indicating a numerical range mean "greater than or equal to A and less than or equal to B" (when A<B), or "less than or equal to A and greater than or equal to B" (when A>B). In other words, descriptions of "from A to B" mean numerical ranges including the endpoints A and B.

Furthermore, the terms "parts by mass" and "mass%" are synonymous with the terms "parts by weight" and "wt.%", respectively.

Compound Represented by Formula (1)

A first aldehyde compound according of the present invention is represented by

Formula (1) below:

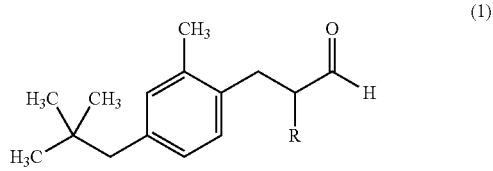

where in Formula (1), R is a hydrogen atom or a methyl group.

In Formula (1), R is a hydrogen atom or a methyl group. Of these, from the perspective of aroma properties, a hydrogen atom is preferable.

The aldehyde compound represented by Formula (1) has an asymmetric carbon when R is a methyl group. In this case, the compound may include only one of optical isomers derived therefrom, or may be a mixture including a plurality of optical isomers in any proportion.

The compound represented by Formula (1) is a novel compound.

The first aldehyde compound represented by Formula (1) has a muguet-tone aroma, which is suitable as a fragrance and a fragrance ingredient, and, in addition, has aromas such as white floral-tone, aldehyde-tone, and green-tone, simultaneously.

The compound represented by Formula (1) is suitable as a fragrance because the compound has an excellent aroma as described below. Generally, a fragrance is rarely used alone, and often used in a fragrance formulation (fragrance composition) produced by formulating a plurality of fragrances in accordance with the purpose. The first aldehyde compound according to an embodiment of the present invention is suitable as a fragrance which is to be blended in a fragrance formulation (fragrance composition) (also referred to as a "fragrance ingredient"). As the fragrance, one of the compounds represented by Formula (1) may be used alone or two of the compounds may be used in combination.

Additionally, the compound represented by Formula (1) of the present invention may include a small amount of impurities, by-products, contaminants, and the like as long as the effects of the present invention are not compromised.

The compound represented by Formula (1) has a muguet-tone aroma as described above as well as an aroma of white floral-tone, aldehyde-tone, green-tone, or the like, and also is excellent in diffusivity.

The compound represented by Formula (1) of the present invention may be used alone as a fragrance and added to various perfumery and cosmetics, healthcare and sanitary materials as well as medicinal supplies, household goods, foods, and the like to thereby impart an aroma or a flavor thereto. Alternatively, the compound represented by Formula (1) of the present invention may be mixed with another fragrance ingredient or the like to prepare a fragrance composition (fragrance formulation) described below, which may be added to a variety of products to impart an aroma or a flavor. Among these, from the perspective of obtaining an intended aroma or flavor, it is preferred that the compound according to an embodiment of the present invention be blended in a fragrance composition as a fragrance ingredient and the fragrance composition be add to a product to perfume the product.

Fragrance Composition

The fragrance composition (fragrance formulation) of the present invention contains the compound represented by Formula (1), which is the first aldehyde compound of the present invention, as an active ingredient. The fragrance composition of the present invention is not particularly limited as long as at least one first aldehyde compound of the present invention is contained, and two first aldehyde compounds of the present invention may be contained. Note that the fragrance is to impart at least either of an aroma and a flavor (hereinafter, "at least either of an aroma and a flavor" is also referred to as "an aroma or the like").

The fragrance composition according to an embodiment of the present invention is only required to contain the first aldehyde compound according to an embodiment of the present invention as an active ingredient, and other ingredients are not particularly limited. However, the fragrance composition preferably contains another fragrance ingredient (hereinafter, also referred to as a "known fragrance").

Note that the "fragrance composition (fragrance formulation)" is a composition that is added to various perfumery and cosmetics, medicinal supplies, foods, beverages, and the like to impart an aroma or the like thereto, or a composition that is used as it is in a perfume or the like. The fragrance composition may contain an additive such as a solvent, as required, in addition to the known fragrance.

The amount of the first aldehyde compound according to an embodiment of the present invention blended depends on the type of the first aldehyde compound according to an embodiment of the present invention, the type of aroma intended, the intensity of the aroma, and the like. The amount of the first aldehyde compound according to an embodiment of the present invention represented by Formula (1) in the fragrance composition is preferably 0.001 mass % or more, more preferably 0.01 mass % or more, even more preferably 0.1 mass % or more, preferably 90 mass % or less, more preferably 70 mass % or less, and even more preferably 50 mass % or less.

The known fragrance is not particularly limited as long as it is a known fragrance component, and a wide range of fragrances can be used. For example, one or two or more of the following fragrances can be selected and used at any mixing ratio.

Examples thereof include hydrocarbons such as limonene, α-pinene, β-pinene, terpinene, cedrene, longifolene, and valencene; alcohols such as linalool, citronellol, geraniol, nerol, terpineol, dihydromyrcenol, ethyllinalool, farnesol, nerolidol, cis-3-hexenol, cedrol, menthol, borneol, β-phenylethyl alcohol, benzyl alcohol, phenyl hexanol, 2,2,6-trimethylcyclohexyl-3-hexanol, 1-(2-t-butylcyclohexyloxy)-2-butanol, 4-isopropylcyclohexane methanol, 4-t-butylcyclohexanol, 4-methyl-2-(2-methylpropyl)tetrahydro-2H-pyran-4-ol, 2-methyl-4-(2,2,3-trimethyl-3-cyclopenten-1-yl)-2-buten-1-ol, 2-ethyl-4-(2,2,3-trimethyl-3-cyclopenten-1-yl)-2-buten-1-ol, isocamphylcyclohexanol, and 3,7-dimethyl-7-methoxyoctane-2-ol; phenols such as eugenol, thymol, and vanillin; esters such as linalyl formate, citronellyl formate, geranyl formate, n-hexyl acetate, cis-3-hexenyl acetate, linalyl acetate, citronellyl acetate, geranyl acetate, neryl acetate, terpinyl acetate, nopyl acetate, bornyl acetate, isobronyl acetate, o-t-butylcyclohexyl acetate, p-t-butylcyclohexyl acetate, tricyclodecenyl acetate, benzyl acetate, styralyl acetate, cinnamyl acetate, dimethylbenzyl-carbinyl acetate, 3-pentyltetrahydropyran-4-yl acetate, citronellyl propionate, tricyclodecenyl propionate, allylcyclohexyl propionate, ethyl-2-cyclohexyl propionate, benzyl propionate, citronellyl butyrate, dim ethylbenzylcarbi nyl n-butyrate, tricyclodecenyl isobutyrate, methyl-2-nonenoate, methyl benzoate, benzyl benzoate, methyl cinnamate, methyl salicylate, n-hexyl salicylate, cis-3-hexenyl salicylate, geranyl tiglate, cis-3-hexenyl tiglate, methyl jasmonate, methyldihydro jasmonate, methyl-2,4-dihydroxy-3,6-dimethyl benzoate, ethylmethylphenyl glycidate, methyl anthranilate, and FRUITATE; aldehydes such as n-octanal, n-decanal, n-dodecanal, 2-methylundecanal, 10-undecenal, citronellal, citral, hydroxycitronellal, dimethyl tetrahydrobenzaldehyde, 4(3)-(4-hydroxy-4-methylpentyl)-3-cyclohexene-l-carboaldehyde, 2-cyclohexyl propanal, p-t-butyl-a-methylhydrocinnamic aldehyde, p-isopropyl-α-methylhydrocinnamic aldehyde, p-ethyl-a,a-dimethylhydrocinnamic aldehyde, α-amylcinnamic aldehyde, α-hexylcinnamic aldehyde, piperonal, and α-methyl-3,4-methylenedioxyhydrocinnamic aldehyde; ketones such as methylheptenone, 4-methylene-3,5,6,6-tetramethyl-2-heptanone, amylcyclopentanone, 3-methyl-2-(cis-2-pentene-1-yl)-2-cyclopenten-1-on, methylcyclopentenolone, rose ketones, γ-methylionone, α-ionone, carbone, menthone, camphor, nootkatone, benzylacetone, anisylacetone, methyl-β-naphthylketone, 2,5-dimethyl-4-hydroxy-3 (2H)-furanone, maltol, 7-acetyl-1,2,3,4,5,6,7,8-octahydro-1, 1,6,7-tetramethyl naphthalene, muscone, civetone, cyclopentadecanone, and cyclohexedecanone; acetals and ketals such as acetaldehyde ethylphenylpropyl acetal, citral diethyl acetal, phenylacetoaldehyde glycerin acetal, and ethyl acetoacetate ethyleneglycol ketals; ethers such as anethole, β-naphthylmethyl ether, β-naphthylethyl ether, limonene oxide, rose oxide, 1,8-cineol, and racemic or photoactive dodecahydro-3a,6,6,9a-tetramethylnaphtho[2, 1-b]furane; nitriles such as citronellyl nitrile; lactones such as γ-nonalactone, γ-undecalactone, σ-decalactone, γ-jasmolactone, coumarin, cyclopentadecanolide, cyclohexadecanolide, ambrettolide, ethylene brassylate, and 11-oxahexadecanolide; and other fragrance materials such as natural essential oils and natural extracts of orange, lemon, bergamot, mandarin, peppermint, spearmint, lavender, chamomile, rosemary, eucalyptus, sage, basil, rose, geranium, jasmine, ylang-ylang, anise, clove, ginger, nutmeg, cardamom, cedar, Japanese cypress, sandalwood, vetiver, patchouli, and labdanum.

In addition, the fragrance composition may also contain, as components besides the fragrance ingredients, a surfactant such as polyoxyethylene lauryl sulfate ether; a solvent such as dipropylene glycol, diethyl phthalate, ethylene glycol, propylene glycol, methyl myristate, triethyl citrate, or the like; an antioxidant such as BHT (ditertiary-butylhydroxytoluene) and vitamin E (tocopherol); a coloring agent, and the like, and preferably contains at least an antioxidant.

The first aldehyde compound according to an embodiment of the present invention represented by Formula (1), which has a muguet-tone aroma and simultaneously has an aroma of a white floral tone, aldehyde tone, green tone, or the like, can impart a natural white floral tone, aldehyde tone, or green note in addition to the muguet tone when combined with a known fragrance. Thus, the first aldehyde compound is suitably added to various perfumery and cosmetics, healthcare and sanitary materials as well as to medicinal supplies, household goods, foods, and the like to thereby impart an aroma or the like thereto.

Examples of products to which a fragrance composition containing the first aldehyde compound according to an embodiment of the present invention represented by Formula (1) can be added to impart an aroma or the like and improve the aroma or the like of the object (product) include various products such as perfumery and cosmetics, health and sanitary materials, miscellaneous goods, beverages, foods, quasi-pharmaceutical products, and medicinal supplies; the fragrance composition can be used as a component for imparting an aroma or the like to, for example, fragrance products such as perfumes and colognes; hair cosmetics such as shampoos, rinses, hair tonics, hair creams, mousses, gels, pomades, sprays, and the like; skin cosmetics such as skin lotions, essences, creams, milky lotions, packs, foundations, face powders, lipsticks, and various make-up products; various health and sanitary detergents such as dish washing detergents, laundry detergents, softeners, disinfecting detergents, anti-odor detergents, indoor fragrances, furniture cares, glass cleaners, furniture cleaners, floor cleaners, disinfectants, insecticides, bleaching agents, bactericides, repellants, and the like; quasi-pharmaceutical products such as toothpastes, mouthwashes, bath additives, antiperspirant products, and perming liquids; miscellaneous goods such as toilet paper and tissue paper; medicinal supplies; foods, and the like.

The amount of the fragrance composition added to the product is not particularly limited, and the amount of the fragrance composition added can be selected over a wide range, depending on the type, nature, and sensory benefits of the product to be perfumed. For example, the amount may be 0.00001 mass % or greater, preferably 0.0001 mass % or greater, more preferably 0.001 mass % or greater. In the case of a fragrance such as perfume or the like, for example, the amount may be 100 mass %, preferably 80 mass % or less, more preferably 60 mass % or less, and even more preferably 40 mass % or less.

Compound Represented by Formula (2)

The second aldehyde compound of the present invention is represented by Formula (2) below.

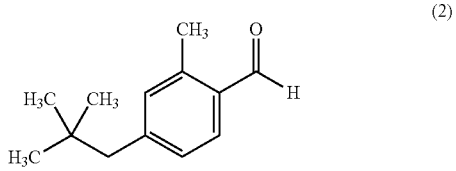

(2)

The compound represented by Formula (2) above is suitable as a synthetic intermediate (or a synthetic raw material) of the first aldehyde compound of the present invention described above.

In addition to the compound represented by Formula (1), a compound suitable as another fragrance is also expected to be synthesized from the compound represented by Formula (2).

A method for synthesizing the compound represented by Formula (1) and a method for using the compound represented by Formula (2) as a synthetic intermediate (or synthetic raw material) of the compound represented by Formula (1) will be described later.

Note that, in the present invention, on synthesis of the compound represented by Formula (1), the compound represented by Formula 2 may include a small amount of impurities, by-products, contaminants, and the like as long as the effects of the present invention are not compromised.

Method for Producing Compound Represented by Formula (2)

In the present invention, the method for producing the compound represented by Formula (2) is not particularly limited. Examples thereof include a method in which 3-neopentyltoluene is allowed to react with carbon monoxide in the presence of triflic acid (trifluoromethanesulfonic acid) under a pressurized condition, but the compound is preferably produced by causing 3-neopentyltoluene to react with carbon monoxide in the presence of hydrogen fluoride and boron trifluoride.

The reaction is specifically represented by the following formula:

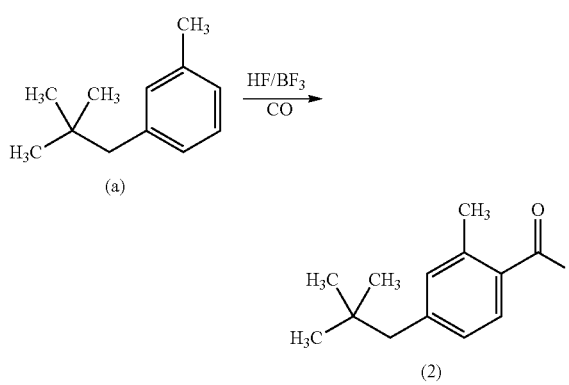

Note that, in the reaction above, the 4-position and 6-position of 3-neopentyltoluene are easily formylated and the 6-position is preferably formylated by improvement in the regioselectivity. The regioselectivity of the formylation depends on the amount of hydrogen fluoride and boron trifluoride relative to 3-neopentyltoluene, the pressure of the carbon monoxide, the reaction time, the reaction temperature, and the like, as described below. Optimizing these enables the regioselectivity to be improved.

Hydrogen fluoride (HF) also has a function as a solvent for the reaction. The hydrogen fluoride is preferably substantially anhydrous hydrogen fluoride from the perspective of the reactivity. Note that the phrase "substantially anhydrous" means that the water content is 5 mass % or less, preferably 1 mass % or less, and more preferably 0.1 mass % or less.

The molar ratio of hydrogen fluoride to 3-neopentyltoluene (hydrogen fluoride/3-neopentyltoluene) is preferably 1.5 or greater, more preferably 3.0 or greater, and even more preferably 5.0 or greater from the perspective of reactivity with carbon monoxide and suppressing side reactions, and is preferably 30.0 or less, more preferably 20.0 or less, and even more preferably 12.0 or less from the perspective of economic efficiency and production efficiency.

The molar ratio of boron trifluoride ($BF_3$) to 3-neopentyltoluene (boron trifluoride/3-neopentyltoluene) is preferably 0.1 or greater, more preferably 0.5 or greater, even more preferably 1.0 or greater, and still even more preferably 1.2 or greater, and is preferably 5.0 or less, more preferably 3.0 or less, and even more preferably 2.0 or less, from the perspective of regioselectively advancing formylation.

The temperature at which carbon monoxide is allowed to react during the reaction is preferably −50° C. or higher, more preferably −40° C. or higher, and preferably 30° C. or lower, more preferably 10° C. or lower, even more preferably 5° C. or lower, from the perspective of improving the reactivity, suppressing side reactions, and improving the selectivity of the position at which the formyl group is introduced.

The reaction between 3-neopentyltoluene and carbon monoxide is preferably performed under pressure.

The pressure during the reaction is preferably 1.0 MPaG or greater, more preferably 1.5 MPaG or greater, and even more preferably 1.8 MPaG or greater, and is preferably 3.0 MPG or less, more preferably 2.5 MPG or less, and even more preferably 2.2 MPaG or less, as a carbon monoxide partial pressure, from the perspective of improving the reactivity and suppressing side reactions.

In the present invention, the reaction time is not particularly limited, and is preferably 10 minutes or more, more preferably 20 minutes or more, and even more preferably 30 minutes or more, and is preferably 24 hours or less, more preferably 12 hours or less, and even more preferably 5 hours or less, from the perspective of sufficiently advancing the reaction, suppressing side reactions and decomposition of products as well as efficient production.

The production method of the present invention may be performed in the presence of a solvent. The solvent to be used is not particularly limited as long as the solvent has good solubility of the reaction raw material and is inert to hydrogen fluoride and boron trifluoride. Examples thereof include saturated aliphatic hydrocarbons such as hexane, heptane, and decane, aromatic hydrocarbons such as benzene and toluene, and halogenated aliphatic hydrocarbons such as chloroform, methylene chloride, and dichloroethane. One type of these solvents may be used alone, or two or more types of these may be used in combination.

The amount of solvent to be used is not particularly limited, and is only required to be selected as appropriate from the perspective of the uniformity of the reaction, reaction rate, and solvent removal.

Note that, in the present invention, the hydrogen fluoride present during the reaction also functions as a solvent, and thus no solvent may be used.

The above reaction may be any method such as a batch type, a semi-batch type, a continuous type, and the like, but is preferably a continuous type, from the perspective that the catalyst can be recovered and recycled and the perspective of production efficiency.

The apparatus to be used in the production method is a reaction apparatus capable of sufficiently mixing the liquid phase and the gas phase while adjusting the temperature under pressure.

For example, in the continuous type, first, hydrogen fluoride and boron trifluoride are placed into a reactor equipped with a stirrer, the contents are stirred, the liquid temperature is set to a suitable temperature, and the temperature is kept constant. Then, the pressure is raised to a suitable reaction pressure with carbon monoxide, and carbon monoxide is allowed to be supplied so that the pressure is kept constant. Thereafter, as necessary, performed is a semi-batch type reaction that supplies 3-neopentyltoluene dissolved in a solvent. Further subsequently, supply of hydrogen fluoride, boron trifluoride, and 3-neopentyltoluene dissolved in a solvent as necessary is started, and the reaction product solution is continuously extracted.

After hydrogen fluoride and boron trifluoride are removed from the reaction solution containing 2-methyl-4-neopentylbenzaldehyde, the reaction solution can be purified by a known method such as distillation or extraction. In order to remove hydrogen fluoride from the reaction solution, neutralization water washing may be performed using an aqueous sodium hydroxide solution.

Note that the compound represented by Formula (a) above (3-neopentyltoluene) may be synthesized as follows.

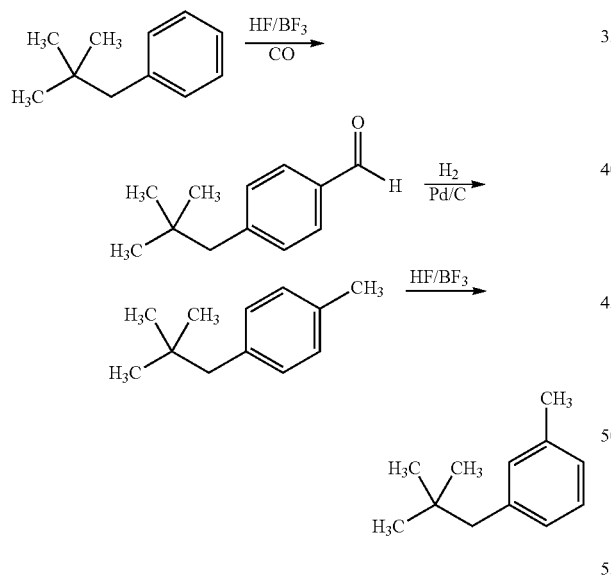

Neopentylbenzene is allowed to react with carbon monoxide in the presence of hydrogen fluoride and boron trifluoride to formylate the p-position of the neopentyl group to produce 4-neopentylbenzaldehyde.

Next, the resulting 4-neopentylbenzaldehyde is reduced in the presence of a palladium catalyst to reduce the formyl group to a methyl group.

Further, in the 4-neopentyltoluene obtained, isomerization reaction is allowed in the presence of hydrogen fluoride and boron trifluoride, and 3-neopentyltoluene generated by the isomerization reaction is isolated to thereby produce 3-neopentyltoluene.

Method for Producing Compound Represented by Formula (1)

The compound represented by Formula (1) may be produced by any method, and examples of the production method include a method in which the 6-position of 3-neopentyltoluene is brominated, allyl alcohol is allowed to react therewith in the presence of a secondary amine and a palladium catalyst, and the propanol side chain of the compound obtained is oxidized. As for the above method, reference is made to JP 2017-533926.

In the present invention, the compound represented by Formula (1) is preferably produced by the following production method. Specifically, the method is a production method including the following steps (i) and (ii) in the order mentioned:

Step (i): performing an aldol condensation on a compound represented by Formula (2) above with acetaldehyde or propionaldehyde to form a compound represented by Formula (3) below; and Step (ii): hydrogenating the compound represented by Formula (3) below to form a compound represented by Formula (1) above.

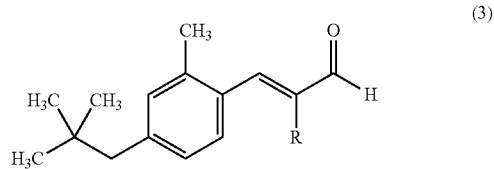

where in Formula (3), R is a hydrogen atom or a methyl group; and

The reaction formula is shown below.

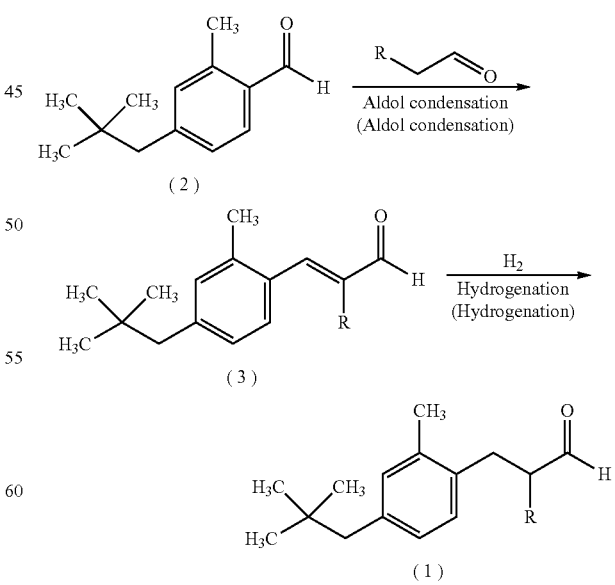

where in Formula (3), R is a hydrogen atom or a methyl group.

Step (i)

Step (i) is a step of performing an aldol condensation on a compound represented by Formula (2) above with acetaldehyde or propionaldehyde to form a compound represented by Formula (3) above.

More specifically, the compound represented by Formula (2) is preferably allowed to react with acetaldehyde or propionaldehyde in the presence of a basic compound as a catalyst.

Examples of the basic compound used as a catalyst include sodium hydroxide, potassium hydroxide, sodium bicarbonate, or a mixture thereof.

The amount of the basic compound is preferably 0.05 equivalent or greater, more preferably 0.1 equivalent or greater, even more preferably 0.2 equivalent or greater, and is preferably 3 equivalents or less, more preferably 1 equivalent or less, even more preferably 0.5 equivalent or less with respect to 1 equivalent of the compound represented by Formula (2).

The amount of acetaldehyde or propionaldehyde added is preferably 1.0 equivalent or greater, more preferably 1.05 equivalents or greater, and preferably 1.5 equivalents or less, more preferably 1.1 equivalents or less, with respect to 1 equivalent of the compound represented by Formula (2).

Acetaldehyde or propionaldehyde is preferably added sequentially or continuously over time, and for example, is preferably added dropwise.

The reaction describe above is preferably performed in a solvent, and examples of the solvent to be used include various water-miscible organic solvents. Specifically, preferable examples thereof include alcohols such as methanol, ethanol, 1-propanol, 2-propanol, tert-butanol, allyl alcohol, ethylene glycol, propylene glycol, and diethylene glycol, and more preferable examples thereof include methanol, ethanol, 1-propanol, 2-propanol, tert-butanol, ethylene glycol, propylene glycol, and diethylene glycol.

The reaction temperature is not particularly limited, is preferably 0° C. or higher, more preferably 3° C. or higher, and even more preferably 5° C. or higher from the perspective of the reaction rate, and is preferably 50° C. or lower, more preferably 40° C. or lower, and even more preferably 30° C. or lower from the perspective of suppressing side reactions.

The reaction time is not particularly limited as long as the condensation is sufficiently performed, and is preferably 10 minutes or more, more preferably 30 minutes or more, and even more preferably 1 hour or more, and is preferably 24 hours or less, more preferably 12 hours or less, even more preferably 6 hours or less, and still even more preferably 3 hours or less.

The reaction is only required to be stopped by neutralization. For example, the reaction is only required to be stopped by addition of an acid such as acetic acid.

In addition, a method for isolating the compound represented by Formula (3) from the reaction solution is not particularly limited, and the isolation may be performed by appropriately combining liquid separation, extraction operation, chromatography, and the like. For example, a low-polar or nonpolar organic solvent is added to the reaction solution, the compound represented by Formula (3) is transferred to the oil phase. The oil phase is dried over, for example, magnesium sulfate. Then the filtrate obtained by filtration is concentrated, and further, purification of the concentrate by column chromatography can isolate the compound.

Step (ii)

Step (ii) is a step of hydrogenating the compound represented by Formula (3) above produced in Step (1) to form a compound represented by Formula (1) above.

The hydrogenation method is not particularly limited, and the hydrogenation can be performed by a known method using a hydrogenation catalyst.

The hydrogenation catalyst is not particularly limited, and a known catalyst can be used. Examples thereof to be used include a supported heterogeneous hydrogenation catalyst in which a metal such as Ni, Pt, Pd, Ru, or the like is supported on carbon, silica, alumina, diatomaceous earth, or the like; a so-called Ziegler-type hydrogenation catalyst for which a transition metal salt including an organic acid salt or an acetylacetone salt such as Ni, Co, Fe, or Cr, or the like, and a reducing agent such as organoaluminum are used; and a homogeneous hydrogenation catalyst such as a so-called organometallic complex including an organometallic compound such as Ti, Ru, Rh, Zr, or the like.

The temperature of the hydrogenation reaction is preferably 0° C. or higher, more preferably 10° C. or higher, and even more preferably 20° C. or higher, and is preferably 200° C. or lower, more preferably 150° C. or lower, even more preferably 100° C. or lower, from the perspective of the reactivity and suppressing side reactions.

The pressure of hydrogen used in the hydrogenation reaction is preferably 0.01 MPaG or greater, more preferably 0.03 MPaG or greater, and even more preferably 0.05 MPaG or greater, and is preferably 10 MPaG or less, more preferably 3 MPaG or less, even more preferably 1 MPaG or less, and still even more preferably 0.5 MPaG or less.

The reaction time is not particularly limited, and is preferably 3 minutes or more, more preferably 10 minutes or more, and even more preferably 30 minutes or more, and is preferably 24 hours or less, more preferably 12 hours or less, and even more preferably 8 hours or less.

The hydrogenation reaction may be performed in the presence of a solvent. The solvent to be used is not particularly limited as long as the hydrogenation reaction is not inhibited, and examples thereof include hydrocarbon solvents including: aliphatic hydrocarbons such as pentane, hexane, isopentane, heptane, octane, and isooctane; cycloaliphatic hydrocarbon such as cyclopentane, methylcyclopentane, cyclohexane, methylcyclohexane, and ethylcyclohexane; and aromatic hydrocarbons such as benzene, toluene, ethylbenzene, and xylene. One type of these may be used alone, or two or more types of these may be used in combination.

The method for isolating and purifying the compound represented by Formula (1) from the reaction solution is not particularly limited, and a known method may be appropriately selected and performed. Specific examples thereof include filtration, chromatography, and distillation, and these may be used in combination as appropriate for purification.

EXAMPLES

The present invention will be described more specifically hereinafter using examples and comparative examples, but the present invention is not limited to these examples.

NMR Spectrum Analysis

Apparatus: JEOL JNM-AL -400 400 MHz (available from JEOL)
Solvent: deuterated chloroform (CDCl$_3$)
Measurement mode: $^1$H, $^{13}$C
Internal standard substance: tetramethylsilane (TMS)

Mass Spectrometry

Apparatus: GCMS-QP 2010 Ultra (available from Shimadzu Corporation)
Ionization method: EI Tone Evaluation The tone (type of scent) of the compound obtained was evaluated by impregnating filter paper having a width of 8 mm and a length of 15 cm with the compound and allowing a specialized panelist to smell the filter paper.

Examples

In the following Examples, when the amount synthesized was insufficient for a raw material of the subsequent synthesis, the same synthesis was repeated a plurality of times to synthesize a necessary amount.

Synthesis of 4-Neopentylbenzaldehyde

As the formylation reactor, used was a 500-mL autoclave equipped with a NAC drive-type stirrer and 3 inlet nozzles at the top and 1 outlet nozzle at the bottom, the internal temperature of which autoclave was controllable with a jacket.

A refrigerant was allowed to flow through the jacket, and the autoclave cooled to −25° C. was charged with 134.2 g (6.71 mol) of hydrogen fluoride.

Thereafter, 70.6 g (1.04 mol) of boron trifluoride was added under stirring while the temperature was adjusted so as not to exceed −25° C.

After boron trifluoride was added, the pressure was raised to 2 MPaG with carbon monoxide while the temperature in the autoclave was maintained at −25° C., and 100.0 g (0.67 mol) of neopentylbenzene (available from Tokyo Chemical Industry Co., Ltd.) was added thereto.

After stirred for 90 minutes while a temperature of −25° C. and a pressure of 2 MPa were maintained, the reaction mixture in the autoclave was extracted into ice water. The mixture extracted was shaken well, and then the oil layer was separated. After the oil layer portion was neutralized and washed with water, the oil layer portion was purified by distillation (131° C., 15 Torr) and 87.5 g (0.50 mol) of 4-neopentylbenzaldehyde was obtained as a colorless transparent liquid.

The structural formula, NMR spectrum, and measurement results of mass spectrometry of the obtained 4-neopentylbenzaldehyde are as follows.

4-Neopentylbenzaldehyde $^1$H NMR (400 MHz, CDCl$_3$) δ 6 0.92 (9H, s), 2.58 (2H, s), 7.28-7.30 (2H, d, J=8.0 Hz), 7.78-7.80 (2H, d, J=8.0 Hz), 9.99 (1H, s)
$^{13}$C NMR (100 MHz, CDCl3) δ 6 29.5, 32.1, 50.4, 129.3, 131.1, 134.5, 147.4, 192.2
MS(EI):m/z (%) 57(50), 91(45), 120(100), 161(10), 176 (M$^+$·, 5)

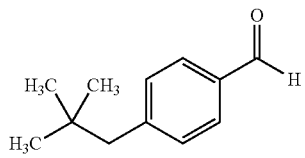

Synthesis of 4-Neopentyltoluene 50.0 g (0.28 mol) of 4-neopentylbenzaldehyde, 25.0 g of heptane, and 2.5 g (5 wt %) of 10% Pd/C were added to a 200-mL autoclave. After the inside of the reactor was purged with nitrogen, hydrogen substitution was conducted. The pressure was raised to 1.0 MPaG with hydrogen and the temperature was raised to 50° C. with stirring. After the temperature was raised, the reaction was performed for 10 hours while the pressure and the temperature were maintained at 1.0 MPaG and 50° C., respectively.

The crude reaction solution was filtered to remove the catalyst, and the filtrate was concentrated with a rotary evaporator. The obtained concentrate was purified by distillation (97° C., 20 Torr) and 33.9 g (0.21 mol) of 4-neopentyltoluene was obtained as a colorless transparent liquid.

The structural formula, NMR spectrum, and measurement results of mass spectrometry of the obtained 4-neopentyltoluene are as follows.

4-Neopentyltoluene $^1$H NMR (400 MHz, CDCl$_3$) δ 0.89 (9H, s), 2.31 (3H, s), 2.45 (2H, s), 6.99-7.02 (2H, d, J=8.4 Hz), 7.05-7.07 (2H, d, J=8.4 Hz)
$^{13}$C NMR (100 MHz, CDCl$_3$) δ 21.2, 29.5, 31.8, 50.0, 128.5, 130.5, 135.2, 136.8
MS(EI):m/z (%) 57(88), 77(12), 91(41), 106(100), 147 (17), 162(M$^+$·, 48)

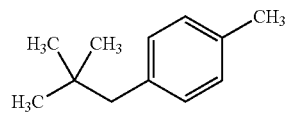

Synthesis of 3-Neopentyltoluene

As the isomerization reactor, used was a 500-mL autoclave equipped with a NAC drive-type stirrer and 3 inlet nozzles at the top and 1 outlet nozzle at the bottom, the internal temperature of which autoclave was controllable with a jacket.

A refrigerant was allowed to flow through the jacket, and the autoclave cooled to 0° C. was charged with 191.5 g (9.57 mol) of hydrogen fluoride.

Thereafter, 47.7 g (0.70 mol) of boron trifluoride was added under stirring while the temperature was adjusted so as not to exceed 15° C.

After boron trifluoride was added, a mixed solution of 38.5 g (0.24 mol) of 4-neopentyltoluene and 38.5 g of hexane was added thereto while the temperature in the autoclave was maintained at 15° C.

After stirring for 4 hours while a temperature of 15° C. was maintained, the reaction mixture in the autoclave was extracted into ice water. After the discharge was shaken well, the oil layer was separated and washed with neutralized water.

These operations were performed three times, and the total of the oil layers was concentrated in a rotary evaporator. The concentrate was purified by distillation (93° C., 20 Torr), and 87.0 g (0.53 mol) of 3-neopentyltoluene was obtained as a colorless transparent liquid.

The structural formula, NMR spectrum, and measurement results of mass spectrometry of the obtained 3-neopentyltoluene are as follows.

3-Neopentyltoluene $^1$H NMR (400 MHz, CDCl$_3$) δ 0.90 (9H, s), 2.33 (3H, s), 2.45 (2H, s), 6.91-6.93(1H, d, J=8.0 Hz), 6.93 (1H, s), 7.00-7.02 (1H, d, J=7.6 Hz), 7.13-7.17 (1H, t, J=7.6 Hz)

$^{13}$C NMR (100 MHz, CDCl$_3$) δ 21.6, 29.6, 31.8, 50.3, 126.6, 127.6, 127.7, 131.4,137.1, 139.8

MS(EI):m/z (%) 57(96), 77(13), 91(45), 106(100), 147 (16), 162(M$^+$·, 48)

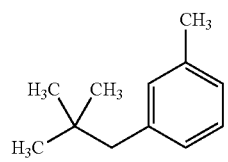

Synthesis of 2-Methyl-4-neopentylbenzaldehyde

As the formylation reactor, used was a 500-mL autoclave equipped with a NAC drive-type stirrer and 3 inlet nozzles at the top and 1 outlet nozzle at the bottom, the internal temperature of which autoclave was controllable with a jacket.

A refrigerant was allowed to flow through the jacket, and the autoclave cooled to −25° C. was charged with 43.0 g (2.15 mol) of hydrogen fluoride.

Thereafter, 29.5 g (0.44 mol) of boron trifluoride was added under stirring while the temperature was adjusted so as not to exceed −25° C.

After boron trifluoride was added, the pressure was raised to 2 MPaG with carbon monoxide while the temperature in the autoclave was maintained at −25° C., and 47.1 g (0.29 mol) of 3-neopentyltoluene and 47.1 g of heptane were added thereto.

After stirred for 120 minutes while a temperature of −25° C. and a pressure of 2 MPa were maintained, the reaction mixture in the autoclave was extracted into ice water. After the discharge was shaken well, the oil layer was separated, and the oil layer portion was washed with neutralized water.

These operations were performed twice, the total of the obtained oil layer portions was concentrated with a rotary evaporator, and the concentrate was purified by distillation (139° C., 15 Torr), and 82.1 g (0.43 mol) of 2-methyl -4-neopentylbenzaldehyde was obtained as a colorless transparent liquid.

The structural formula, NMR spectrum, and measurement results of mass spectrometry of the obtained 2-methyl-4-neopentylbenzaldehyde are as follows.

2-Methyl-4-neopentylbenzaldehyde $^1$H NMR (400 MHz, CDCl$_3$) δ 0.92 (9H, s), 2.52 (2H, s), 2.65 (3H, s), 7.01 (1H, s), 7.11-7.13 (1H, d, J=7.6 Hz), 7.69-7.71 (1H, d, J=7.6 Hz), 10.23 (1H, s)

$^{13}$C NMR (100 MHz, CDCl$_3$) δ 19.7, 29.5, 32.1, 50.3, 128.5, 131.8, 132.3, 133.9, 139.9, 146.4, 192.5

MS(EI):m/z (%) 57(65), 77(8), 91(26), 105(40), 134 (100), 175(11), 190(M$^+$·, 29)

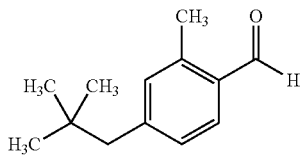

Synthesis of (E)-3-(2-Methyl-4-Neopentylphenyl)Propenal

To a 100-mL round-bottom flask, 15.0 g (0.08 mol) of 2-methyl-4-neopentylbenzaldehyde, 15 g of methanol as a solvent, and 2.1 g (0.03 mol) of a 50% aqueous NaOH solution as a catalyst were added and cooled to 10° C.

Thereafter, 3.9 g (0.09 mol) of acetaldehyde was added dropwise under stirring while the temperature was adjusted so as not to exceed 15° C. After 2 hours of the reaction, 2.0 g (0.03 mol) of acetic acid was added for quenching.

After the quenching, extraction and liquid separation operations were performed using heptane, the oil layer portion was dried over magnesium sulfate, and the filtrate obtained by filtration was concentrated with a rotary evaporator.

The concentrate produced was purified by column chromatography (silica gel, hexane: ethyl acetate=9:7), and 5.0 g (0.02 mol) of (E)-3-(2-methyl-4-neopentylphenyl)propenal was obtained as a yellow solid.

The structural formula, NMR spectrum, and measurement results of mass spectrometry of the (E)-3-(2-methyl-4-neopentylphenyl)propenal obtained are as follows.

(E)-3-(2-Methyl-4-neopentylphenyl)propenal $^1$H NMR (400 MHz, CDCl$_3$) δ 0.92 (9H, s), 2.47 (3H, s), 2.49 (2H, s), 6.63-6.69(1H, dd, J=7.6 Hz, 16 Hz), 7.01 (1H, s), 7.01-7.03 (1H, d, J=9.6 Hz), 7.51-7.53 (1H, d, J=7.6 Hz), 7.74-7.78 (1H, d, J=16 Hz), 9.70-9.72 (1H, d, J=7.6 Hz)

$^{13}$C NMR (100 MHz, CDCl$_3$) δ 19.9, 29.6, 32.1, 50.2, 126.3, 128.8, 129.0, 130.5, 133.3, 137.4, 143.7, 150.6, 194.1

MS(EI):m/z (%) 57(71), 91(11), 115(16), 131(17), 145 (100), 160(70), 201(29), 216(M$^+$·, 16)

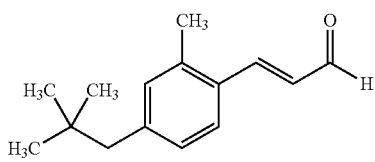 [SMILES: Cc1cc(CC(C)(C)C)ccc1/C=C/C=O]

Synthesis of 3-(2-Methyl-4-Neopentylphenyl)Propanal 0.7 g (0.003 mol) of (E)-3-(2-methyl-4-neopentylphenyl) propenal, 35.0 g of heptane as a solvent, and 0.07 g (10 wt %) of 10% Pd/C as a catalyst were added in a 200-mL autoclave. After the inside of the reactor was purged with nitrogen, hydrogen substitution was conducted. Thereafter, the pressure was raised to 0.1 MPaG with hydrogen, and the mixture was stirred. After the pressure was raised, the reaction was performed for 1 hour while the pressure and the temperature were maintained at 0.1 MPaG and 25° C., respectively.

The crude reaction solution obtained was filtered to remove the catalyst, and the filtrate was concentrated with a rotary evaporator. The concentrate was purified by column chromatography (silica gel, hexane: ethyl acetate=96:4), and 0.4 g (0.002 mol) of 3-(2-methyl-4-neopentylphenyl)propanal was obtained as a colorless transparent liquid.

The structural formula, NMR spectrum, measurement results of mass spectrometry, and tone of the obtained 3-(2-methyl-4-neopentylphenyl) propanal are as follows.

3-(2-Methyl-4-neopentylphenyl)propanal $^1$H NMR (400 MHz, CDCl$_3$) δ 0.89 (9H, s), 2.29 (3H, s), 2.42 (2H, s), 2.71-2.75 (2H, t, J=7.8 Hz), 2.90-2.94 (2H, t, J=7.8 Hz), 6.89-6.91 (1H, d, J=7.6 Hz), 6.91 (1H, s), 7.00-7.02 (1H, d, J=7.2 Hz), 9.85 (1H, s)

$^{13}$C NMR (100 MHz, CDCl$_3$) δ 19.5, 25.2, 29.5, 31.8, 44.2, 49.8, 127.8, 128.4, 132.7, 135.1, 135.7, 138.0, 202.0

MS(EI):m/z (%) 57(100), 77(7), 91(19), 105(19), 118 (57), 129(28), 144(90), 162(25), 203(8), 218(M$^+$, 30)

Tone: muguet, white floral, aldehyde, green

Note that the tone had a marine fatty note slightly stronger than that of lilial and was a tone like an intermediate between lilial and silvial.

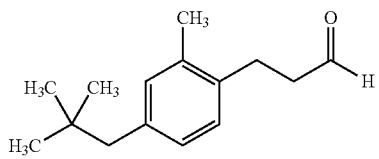 [SMILES: Cc1cc(CC(C)(C)C)ccc1CCC=O]

Synthesis of (E) -3 -(2-Methyl-4-neopentylphenyl)-2-Propenal

To a 100 mL round-bottom flask, 15.0 g (0.08 mol) of 2-methyl-4-neopentylbenzaldehyde, 15.0 g of methanol as a solvent, and 2.0 g (0.03 mol) of a 50% aqueous NaOH solution as a catalyst were added and maintained at 25° C.

Thereafter, 5.0 g (0.09 mol) of propionaldehyde was added dropwise under stirring while the temperature was adjusted so as not to exceed 25° C. After 2 hours of the reaction, 1.6 g (0.03 mol) of acetic acid was added thereto for quenching.

After the quenching, extraction and liquid separation operations were performed using heptane, the oil layer portion was dried over magnesium sulfate, and the filtrate by filtration was concentrated with a rotary evaporator.

The obtained concentrate was purified by column chromatography (silica gel, hexane : ethyl acetate=95 : 5), and 13.3 g (0.06 mol) of (E)-3-(2-methyl-4-neopentylphenyl)-2-methylpropenal was obtained as a yellow liquid.

The structural formula, NMR spectrum, and measurement results of mass spectrometry of the obtained (E)-3-(2-methyl-4-neopentylphenyl) -2-methylpropenal are as follows.

(E)-3-(2-Methyl-4-neopentylphenyl)-2-methylpropenal $^1$H NMR (400 MHz, CDCl$_3$) δ 0.93 (9H, s), 1.98 (3H, s), 2.35 (3H, s), 2.49 (2H, s), 7.01-7.03 (1H, d, J=6.4 Hz), 7.03 (1H, s), 7.28-7.30 (1H, d, J=8.4 Hz), 7.43 (1H, s), 9.63 (1H, s)

$^{13}$C NMR (100 MHz, CDCl$_3$) δ 11.0, 19.9, 29.4, 31.8, 50.0, 127.9, 128.3, 131.4, 132.6, 136.5, 138.5, 141.3, 148.3, 195.5

MS(EI):m/z (%) 57(56), 91(7), 105(7), 115(10), 128(12), 145(11), 159(100), 174(33), 215(46), 230(M$^+$, 12)

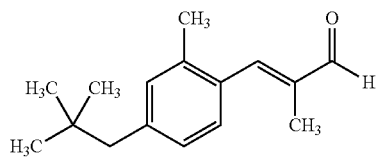

Synthesis of 3-(2-Methyl-4-Neopentylphenyl) -2-Methylpropanal 13.3 g (0.06 mol) of (E) -3-(2-methyl-4-neopentylphenyl) -2 methylpropenal, 40.0 g of a 5 wt % aqueous Na 2 CO 3 solution, and 0.3 g (2 wt %) of 5% Pd/C were added in a 200-mL autoclave. After the inside of the reactor was purged with nitrogen, hydrogen substitution was conducted. Thereafter, the pressure was raised to 0.4 MPaG with hydrogen, and the temperature was raised to 75° C. with stirring. After the temperature was raised, the reaction was performed for 7 hours while the pressure and the temperature were maintained at 0.4 MPaG and 75° C., respectively.

The obtained crude reaction solution was filtered to remove the catalyst, and the filtrate was concentrated with a rotary evaporator. The obtained concentrate was purified by column chromatography (silica gel, hexane:ethyl acetate=96: 4) and then purified by distillation (102° C., 1 Torr), and 6.7 g (0.03 mol) of 3-(2-methyl-4-neopentylphenyl)-2-methylpropanal was obtained as a colorless transparent liquid.

The structural formula, NMR spectrum, measurement results of mass spectrometry, and tone of the obtained 3-(2-methyl-4-neopentylphenyl) -2-methylpropanal are as follows.

3-(2-Methyl-4-neopentylphenyl)-2-methylpropanal $^1$H NMR (400 MHz, CDCl$_3$) δ 0.89 (9H, s), 1.10-1.12 (3H, d, J=6.8 Hz), 2.29 (3H, s), 2.43 (2H, s), 2.54-2.57 (1H, dd, J=8.4 Hz, 14.0 Hz), 2.63-2.68 (1H, m), 3.05-3.10 (1H, dd, J=6.0 Hz, 14.0 Hz), 6.89-6.91 (1H, d, J=7.6 Hz), 6.92 (1H, s), 6.99-7.01 (1H, d, J=7.6 Hz), 9.72 (1H, s) $^{13}$C NMR (100 MHz, CDCl$_3$) δ 13.6, 19.6, 29.5, 31.8, 33.7, 47.0, 49.8, 128.2, 129.0, 032.8, 134.4, 135.3, 138.0, 204.7

MS(EI):m/z (%) 57(93), 77(6), 91(12), 105(27), 119 (100), 131(8), 143(24), 158(64), 175(25), 214(8), 232(M$^+$, 38)

Tone: muguet, white floral, green, woody

Note that the tone had a marine fatty feeling and an aldehyde feeling weaker than those of lilial, and correspondingly, was slightly woody-amber-like and a clean muguet note. It was sensed that the compound has a very large potential in terms of tone.

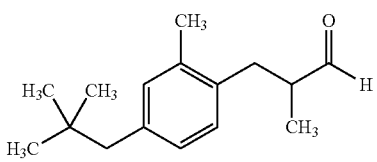 [SMILES: Cc1cc(CC(C)(C)C)ccc1CC(C)C=O]

Fragrance Formulation Evaluation -1

The evaluation results of the tone revealed that 3-(2-methyl-4-neopentylphenyl) propanal had a lilial-like and silvial-like tone. Thus, the following three formulations, which are model formulations of lilial, were evaluated after 3-(2-methyl -4 neopentylphenyl)propanal was added thereto instead of lilial.

Formulations 1 to 3 are shown in the table below. Note that Formulation 1 has a floral powdery-type tone, Formulation 2 has a muguet-type tone, and Formulation 3 has a fruity-floral-type tone.

TABLE 1

| No. | Component | parts by mass |
|---|---|---|
| | Formulation 1 | |
| 1 | ACETYL ISO EUGENOL | 8 |
| 2 | ALDEHYDE C-14 | 8 |
| 3 | BACDANOL | 25 |
| 4 | BENZYL ACETATE | 6 |
| 5 | BENZYL SALICYLATE | 60 |
| 6 | CITRONELLOL | 10 |
| 7 | COUMARIN | 40 |
| 8 | CYCLAMEN ALDEHYDE | 15 |
| 9 | D.M.B.C. ACETATE | 3 |
| 10 | DIHYDRO MYRCENOL | 50 |
| 11 | DIPHENYL OXIDE | 3 |
| 12 | ETHYL LINALOOL | 35 |
| 13 | GERANIOL | 8 |
| 14 | HABANOLIDE | 50 |
| 15 | HEDIONE | 100 |
| 16 | HELIONAL | 4 |
| 17 | HELIOTROPINE | 5 |
| 18 | LEMON OIL ITALY | 10 |
| 19 | METHYL IONONE GAMMA | 40 |
| 20 | MUSK 50 IPM | 120 |
| 21 | PHENYL ETHYL ALCOHOL | 20 |
| 22 | ROSACETOL | 5 |
| 23 | TERPINYL ACETATE | 5 |
| 24 | VANILLIN | 10 |
| 25 | VERTENEX | 40 |
| 26 | LILIAL | 320 |
| | Total | 1000 |
| | Formulation 2 | |
| 1 | BENZYL ACETATE | 20 |
| 2 | BERGAMOT OIL FREE | 30 |
| 3 | CINNAMIC ALCOHOL | 40 |
| 4 | CIS-3-HEXENOL | 3 |
| 5 | CIS-3-HEXENYL ACETATE | 2 |
| 6 | CIS-3-HEXENYL SALICYLATE | 20 |
| 7 | CITRONELLOL | 80 |
| 8 | DPG | 108 |
| 9 | FLOROL | 70 |
| 10 | HEDIONE | 100 |
| 11 | HELIONAL | 10 |
| 12 | HYDROXYCITRONELLAL | 40 |
| 13 | INDOLE PURE | 2 |
| 14 | LINALOOL | 50 |
| 15 | PHENYL ETHYL ALCOHOL | 60 |
| 16 | ROSE OIL BULGARIAN | 2 |

TABLE 1-continued

| No. | Component | parts by mass |
|---|---|---|
| 17 | STEMONE | 3 |
| 18 | YLANG YLANG EXTRA COMOR | 10 |
| 19 | LILIAL | 350 |
| | Total | 1000 |
| | Formulation 3 | |
| 1 | ALDEHYDE C-10 | 2 |
| 2 | ALDEHYDE C-11 UNDECYLIC | 2 |
| 3 | ALDEHYDE C-14 | 20 |
| 4 | ALLYL AMYL GLYCOLATE | 2 |
| 5 | AMBERONE | 60 |
| 6 | AMYL SALICYLATE | 10 |
| 7 | BENZALDEHYDE | 1 |
| 8 | BENZYL ACETATE | 20 |
| 9 | CIS-3-HEXENYL ACETATE | 4 |
| 10 | CITRONELLOL | 10 |
| 11 | CYCLAPROP | 10 |
| 12 | D.M.B.C. ACETATE | 4 |
| 13 | DAMASCONE DELTA | 4 |
| 14 | DECALACTONE GAMMA | 6 |
| 15 | DIMETHYL ANTHRANILATE | 1 |
| 16 | DPG | 84 |
| 17 | HEXYL ACETATE | 10 |
| 18 | HEXYL CINNAMIC ALDEHYDE | 140 |
| 19 | IONONE BETA | 2 |
| 20 | LIGUSTRAL | 10 |
| 21 | LINALOOL | 45 |
| 22 | MANZANATE | 60 |
| 23 | METHYL CINNAMATE | 1 |
| 24 | METHYL IONONE GAMMA | 20 |
| 25 | METHYL PHENYL ACETATE | 1 |
| 26 | NONALACTONE GAMMA | 2 |
| 27 | ORANGE TERPENES | 250 |
| 28 | PARA CRESOL METHYL ETHER | 1 |
| 29 | PRENYL ACETATE | 5 |
| 30 | ROSE OXIDE | 6 |
| 31 | STYRALLYL ACETATE | 6 |
| 32 | UNDECAVERTOL | 1 |
| 33 | VERDOX | 100 |
| 34 | VERTENEX | 50 |
| 35 | LILIAL | 50 |
| | Total | 1000 |

Formulation 1: Examples 1-1 and 1-2

In Example 1-1, a fragrance formulation was produced in the same manner except that 320 parts by mass of 3-(2-methyl-4-neopentylphenyl)propanal were added instead of 320 parts by mass of lilial in Formulation 1, and the tone of thereof was evaluated.

In addition, in Example 1-2, a fragrance formulation was produced in the same manner except that 120 parts by mass of 3-(2-methyl-4-neopentylphenyl)propanal and 200 parts by mass of dipropylene glycol were added instead of 320 parts by mass of lilial in Formulation 1, and the tone of thereof was evaluated. That is, in Example 1-2, the evaluation was conducted while the amount added was reduced to 37.5% of lilial.

Note that dipropylene glycol is odorless and is added for diluting 3-(2-methyl-4-neopentylphenyl)propanal.

Formulation 2: Examples 2-1 and 2-2

In Example 2-1, a fragrance formulation was produced in the same manner except that 350 parts by mass of 3-(2-methyl-4 neopentylphenyl)propanal were added instead of 350 parts by mass of lilial in Formulation 2, and the tone of thereof was evaluated.

In addition, in Example 2-2, a fragrance formulation was produced in the same manner except that 150 parts by mass of 3-(2-methyl-4-neopentylphenyl)propanal and 200 parts by mass of dipropylene glycol were added instead of 350 parts by mass of lilial in Formulation 2, and the tone of thereof was evaluated. That is, in Example 2-2, the evaluation was conducted while the amount added was reduced to 42.9% of lilial.

Formula 3: Examples 3-1 and 3-2

In Example 3-1, a fragrance formulation was produced in the same manner except that 50 parts by mass of 3-(2-methyl-4 neopentylphenyl)propanal were added instead of 50 parts by mass of lilial in Formulation 3, and the tone of thereof was evaluated.

In addition, in Example 3-2, a fragrance formulation was produced in the same manner except that 20 parts by mass of 3-(2-methyl-4-neopentylphenyl)propanal and 30 parts by mass of dipropylene glycol were added instead of 50 parts by mass of lilial in Formulation 3, and the tone of thereof was evaluated. That is, in Example 3-2, the evaluation was conducted while the amount added was reduced to 40% of lilial.

Tone Evaluation

The formulations 1 to 3 described above each were diluted 10 times with 9000 parts of triethyl citrate, and the tone of the fragrance formulations was evaluated.

The tone was evaluated by impregnating filter paper having a width of 8 mm and a length of 15 cm with the compound and allowing a specialized panelist to smell the filter paper.

As a result of evaluating the fragrance tone of the fragrance formulations, and as a result of comparison of the fragrance formulations produced in Examples 1-1, 2-1, and 3-1, with Formulations 1, 2, and 3, respectively, the tone similar to those of Formulations of 1, 2, and 3, which each are a fragrance formulation including lilial added was felt, but the intensity of the scent was stronger.

In addition, as a result of evaluation of the tone in each of Examples 1-2, 2-2, and 3-2, in which the amount added was reduced, felt was a scent having intensity comparable to that in the case where lilial was added. It was shown that 3-(2-methyl-4-neopentylphenyl) propanal was a fragrance having an excellent potency than that of lilial.

Evaluation of Lasting Scent

The lasting scent was evaluated by comparison with lilial. A site 1 cm from the tip of filter paper having a width of 8 mm and a length of 15 cm was impregnated with each of 3-(2-methyl-4 neopentylphenyl) propanal and lilial, and the intensity of the scent immediately after the impregnation was evaluated. Thereafter, the filter paper was left at room temperature, and the intensity of each scent after 6 hours and 18 hours was evaluated.

As a result of evaluation of the lasting scent, 3-(2-methyl-4-neopentylphenyl) propanal had a substantial scent even after 6 hours, and the scent was felt more intense than that of lilial. After 18 hours, 3-(2-methyl-4-neopentylphenyl) propanal had a scent, whereas the scent of lilial was very weak and scarcely perceivable.

Fragrance Formulation Evaluation -2

JP 2018-138550A describes the following compound (hereinafter, nympheal) as an alternative fragrance of lilial.

Thus, the following two formulations, which are the model formulations of nympheal, were evaluated after 3-(2-methyl-4-neopentylphenyl) propanal was added thereto instead of nympheal.

Formulations 4 and 5 are shown in the table below. Note that Formulation 4 has a green-floral tone, and Formulation 5 has a floral-fruity tone.

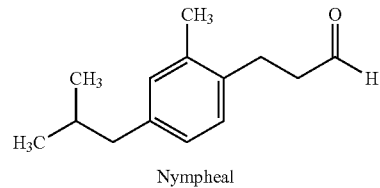

Nympheal

TABLE 2

| No. | Component | parts by mass |
|---|---|---|
| Formulation 4 | | |
| 1 | AMBERON | 20 |
| 2 | AMBROXAN | 0.1 |
| 3 | BACDANOL | 20 |
| 4 | BORNEOL LEAEVO CRIST | 0.1 |
| 5 | CIS JASMONE | 1.2 |
| 6 | CIS-3-HEXENOL | 8 |
| 7 | CIS-3-HEXENYL ACETATE | 2 |
| 8 | CITRAL DIMETHYL ACETAL | 0.4 |
| 9 | CITRAL SYNTH | 0.2 |
| 10 | CITRONELLAL | 0.1 |
| 11 | CITRONELLOL | 25 |
| 12 | DEHYDRO MYRCENOL | 30 |
| 13 | DPG | 128.6 |
| 14 | ETHYLENE BRASSYLATE | 80 |
| 15 | FLOROL | 35 |
| 16 | GERANIOL | 18 |
| 17 | HEDIONE | 200 |
| 18 | IONONE BETA | 30 |
| 19 | LIGUSTRAL | 0.2 |
| 20 | LINALOOL | 100 |
| 21 | GALAXOLIDE 50 IPM | 120 |
| 22 | PHENYL ETHYL ALCOHOL | 60 |
| 23 | ROSE OXIDE | 1 |
| 24 | STYRALLYL ALCOHOL | 0.1 |
| 25 | VERDOX | 70 |
| 26 | NYMPHEAL | 50 |
| Total | | 1000 |
| Formulation 5 | | |
| 1 | ALDEHYDE C-10 | 4 |
| 2 | ALLYL CAPROATE | 4 |
| 3 | BENZYL ACETATE | 15 |
| 4 | CIS JASMONE | 0.4 |
| 5 | CITRONELLOL | 30 |
| 6 | CYCLAMEN ALDEHYDE | 20 |
| 7 | CYCLAPROP | 25 |
| 8 | D.M.B.C. ACETATE | 1.5 |
| 9 | DIPHENYL OXIDE | 0.4 |
| 10 | DPG | 270.7 |
| 11 | ETHYL SALICYLATE | 0.4 |
| 12 | FLORALOZONE | 8 |
| 13 | FOLIONE | 0.2 |
| 14 | GERANIOL | 20 |
| 15 | GERANYL ACETATE | 40 |
| 16 | HELIONAL | 4 |
| 17 | HEXYL ACETATE | 4 |
| 18 | HEXYL CINNAMIO ALDEHYDE | 80 |
| 19 | HEXYL SALICYLATE | 40 |
| 20 | IONONE BETA | 20 |
| 21 | JASMACYOLENE | 45 |
| 22 | LINALOOL | 80 |
| 23 | MANZANATE | 0.8 |

TABLE 2-continued

| No. | Component | parts by mass |
|---|---|---|
| 24 | MELONAL | 0.8 |
| 25 | METHYL IONONE GAMMA | 35 |
| 26 | PHENYL ETHYL ALCOHOL | 50 |
| 27 | STYRALLYL ACETATE | 20 |
| 28 | UNDECAVERTOL | 0.8 |
| 29 | NYMPHEAL | 180 |
|  | Total | 1000 |

Formulation 4: Example 4

In Example 4, a fragrance formulation was produced in the same manner except that 50 parts by mass of 3-(2-methyl-4 neopentylphenyl)propanal were added instead of 50 parts by mass of nympheal in Formulation 4, and the tone of thereof was evaluated.

Formulation 5: Example 5

In Example 5, a fragrance formulation was produced in the same manner except that 180 parts by mass of 3-(2-methyl-4 neopentylphenyl)propanal were added instead of 180 parts by mass of nympheal in Formulation 5, and the tone of thereof was evaluated.

Tone Evaluation

The tone of the fragrance formulation was evaluated in the above formulations 4 and 5.

The tone was evaluated by impregnating filter paper having a width of 8 mm and a length of 15 cm with the compound and allowing a specialized panelist to smell the filter paper.

As a result of evaluating the fragrance tone of the fragrance formulations, and as a result of comparison of the fragrance formulations produced in Example 4 and Example 5, with Formulation 4 and Formulation 5, respectively, the impact and intensity of the middle note were excellent in Examples 4 and 5. More specifically, after 30 minutes to about 3 hours, a solid and strong green-floral feeling was more strongly observed.

Industrial Applicability

The compound represented by Formula (1) of the present invention is suitable as a fragrance (raw material of fragrance formulation) and is expected to be used as an alternative fragrance for lilial. Furthermore, it was revealed that the compound represented by Formula (1) of the present invention is a fragrance having an excellent potency and lasting scent compared to those of the lilial. In addition, even compared with nympheal, which is another alternative fragrance of lilial, it was revealed that the compound has a particularly excellent intensity of the middle note and was an excellent fragrance.

The invention claimed is:

1. A compound represented by Formula (1):

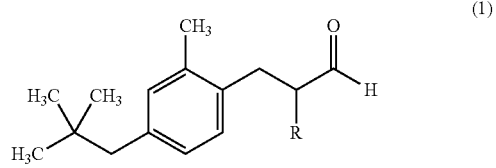

where, in Formula (1), R is a hydrogen atom or a methyl group.

2. The compound according to claim 1, wherein R is a hydrogen atom.

3. A fragrance composition, comprising:
the compound of claim 1.

4. A compound represented by Formula (2):

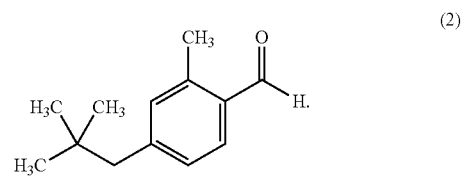

5. A method for producing a compound represented by Formula (1), the method comprising, in this order:

performing an aldol condensation on a compound represented by Formula (2) with acetaldehyde or propionaldehyde to form a compound represented by Formula (3); and hydrogenating the compound represented by Formula (3) to form the compound represented by Formula (1):

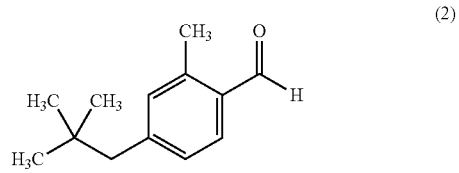

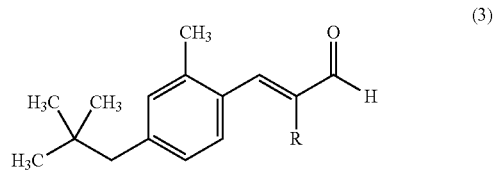

where, in Formula (3), R is a hydrogen atom or a methyl group, and
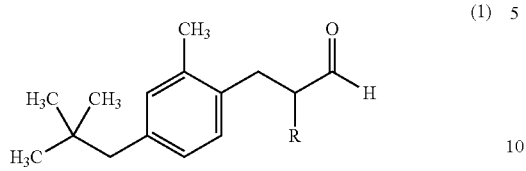
(1)
where, in Formula (1), R is a hydrogen atom or a methyl group.
6. A fragrance composition, comprising: the compound of claim 2.
* * * * *